(12) United States Patent
Shimizu et al.

(10) Patent No.: US 7,474,018 B2
(45) Date of Patent: Jan. 6, 2009

(54) RECIPROCATION TYPE LINEAR DRIVING ACTUATOR AND POWER TOOTHBRUSH USING THE SAME

(75) Inventors: Hiroaki Shimizu, Hikone (JP); Ryo Motohashi, Hikone (JP); Hidekazu Yabuuchi, Hikone (JP); Takahiro Nishinaka, Omihachiman (JP)

(73) Assignee: Panasonic Electric Works Co., Ltd., Osaka (JP)

( * ) Notice: Subject to any disclaimer, the term of this patent is extended or adjusted under 35 U.S.C. 154(b) by 251 days.

(21) Appl. No.: 10/557,253

(22) PCT Filed: May 14, 2004

(86) PCT No.: PCT/JP2004/006556

§ 371 (c)(1),
(2), (4) Date: Nov. 16, 2005

(87) PCT Pub. No.: WO2004/102775

PCT Pub. Date: Nov. 25, 2004

(65) Prior Publication Data

US 2007/0040457 A1    Feb. 22, 2007

(30) Foreign Application Priority Data

May 16, 2003    (JP) .............................. 2003-139571

(51) Int. Cl.
*H02K 41/00*    (2006.01)
(52) U.S. Cl. .............................. 310/12; 310/15; 310/17; 310/216
(58) Field of Classification Search .................... 310/12, 310/17, 15, 216
See application file for complete search history.

(56) References Cited

U.S. PATENT DOCUMENTS 5,934,908 A * 8/1999 Woog et al. .................. 433/216

(Continued)

FOREIGN PATENT DOCUMENTS

JP    7-030585    6/1995

(Continued)

OTHER PUBLICATIONS

English Language Abstract of JP 2002-176758.

(Continued)

*Primary Examiner*—Nicholas Ponomarenko
*Assistant Examiner*—Iraj A Mohandesi
(74) *Attorney, Agent, or Firm*—Greenblum & Bernstein, P.L.C.

(57) ABSTRACT

In a reciprocal linear driving actuator used as a drive source of a power toothbrush, two permanent magnets are formed substantially disc shape or substantially tubular shape, and fitted to and fixed on a shaft directly or via a spacer with a predetermined distance in axial direction of the shaft, so that a moving object is constituted by the shaft and the permanent magnets. On the other hand, a tubular shaped stator, which is constituted by a coil wound around a bobbin and stationary yokes and so on, is provided to face side faces of the permanent magnets of the moving object via a predetermined clearance so that a center axis thereof becomes coaxial with the center axis of the shaft. By supplying alternating current to the coil, the moving object is driven reciprocally and linearly in the axial direction of the shaft.

13 Claims, 11 Drawing Sheets

U.S. PATENT DOCUMENTS 6,833,639 B2 * 12/2004 Lau et al. .................. 310/36
2005/0235438 A1 10/2005 Motohashi et al.
2006/0010622 A1 1/2006 Naruse et al.

FOREIGN PATENT DOCUMENTS

| JP | 9-173360 | 7/1997 |
|---|---|---|
| JP | 2002-176758 | 6/2002 |
| JP | 2002-218727 | 8/2002 |

OTHER PUBLICATIONS

English Language Abstract of JP 9-173360.
English Language Abstract of JP 2002-218727.
English Language Abstract of JP 7-030585.
U.S. Appl. No. 10/557,255 to Shimizu et al., filed Nov. 16, 2005.
U.S. Appl. No. 10/557,252 to Shimizu et al., filed Nov. 16, 2005.

* cited by examiner

RECIPROCATION TYPE LINEAR DRIVING ACTUATOR AND POWER TOOTHBRUSH USING THE SAME

TECHNICAL FIELD

The present invention relates to a reciprocation type linear driving actuator and a power toothbrush using the same.

BACKGROUND ART

Figure 15:
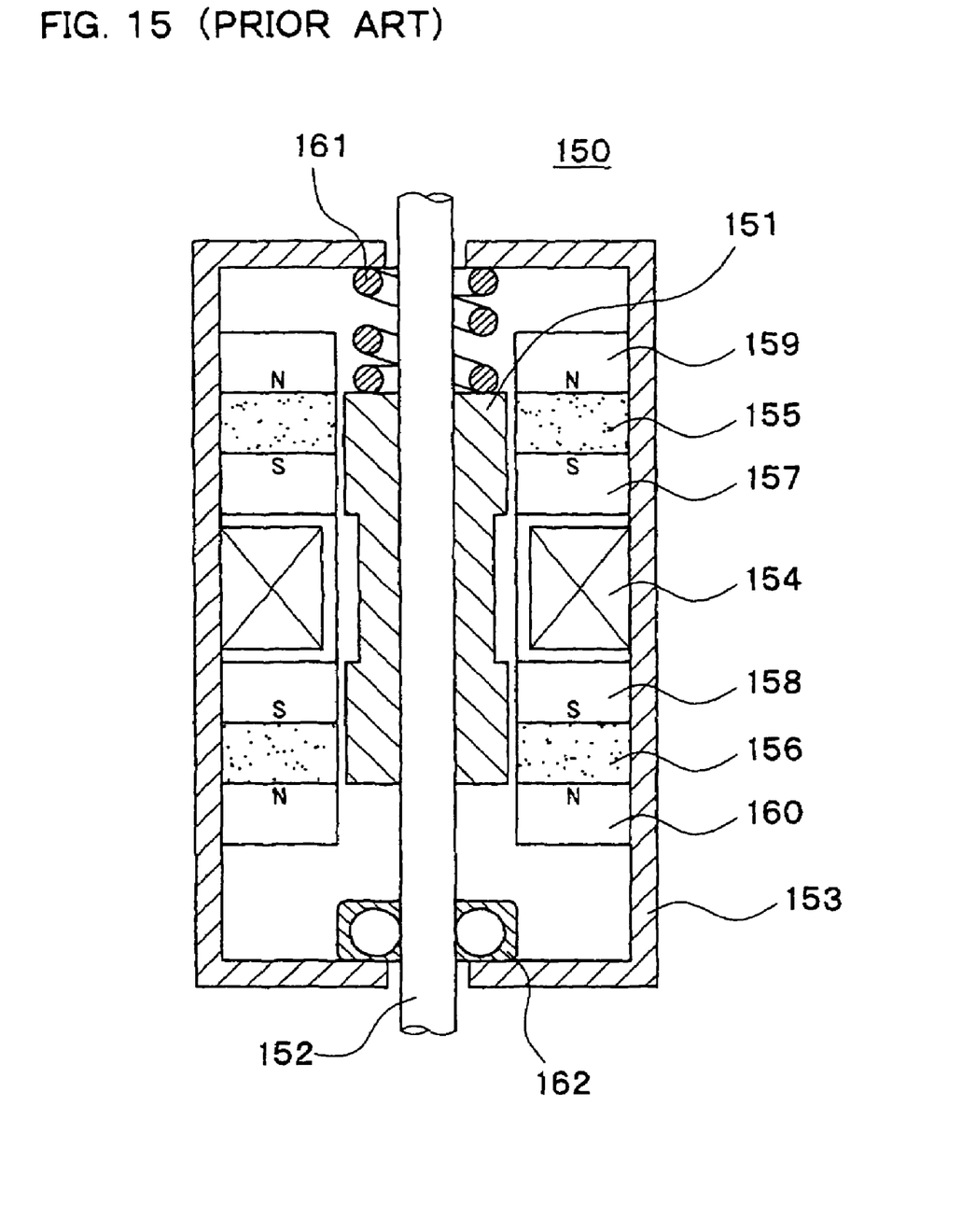
FIG. 15 is a sectional view showing a configuration of a conventional reciprocation type linear driving actuator.

A conventional reciprocation type linear driving actuator, for example, shown in Japanese Laid-Open Patent Publication No. 2002-176758 is explained referring to FIG. 15. In this conventional reciprocation type linear driving actuator 150, a plunger 151 formed of a magnetic material is fixed on an outer periphery of a shaft 152. The shaft 152 is pivoted by a bearing 162 capable of reciprocally and linearly moving in a direction (axial direction) parallel to the center axis thereof. A ring shaped coil 154 is disposed on an inner peripheral surface of a shielding case 153 with a predetermined clearance with respect to the outer periphery of the plunger 151. Furthermore, ring shaped permanent magnets 155 and 156 which are magnetized in symmetrical with respect to the coil 154 are disposed on the inner peripheral surface of the shielding case 153 and on both sides of the coil 154 in the above axial direction. Ring shaped first yokes 157 and 158 are respectively disposed between the permanent magnets 155 and 156 and the coil 154, and ring shaped second yokes 159 and 160 are disposed at positions opposite to the permanent magnets 155 and 156 with respect to the coil 154. A spring member 161 is disposed between the plunger 151 and the shielding case 152 (SIC: correctly 153) for applying an accompanying force to the plunger 151 in a one direction among the reciprocation directions of linear driving.

When no current flows in the coil 154, the plunger 151 is stopped at a position where magnetic forces applied to the plunger 151 by two permanent magnets 155 and 156 via the yokes 157 and 158 is balanced with a pressing force due to the spring member 61 (SIC: correctly 161). When a unidirectional current flows in the coil 154, magnetic flux due to one of the permanent magnets 155 and 156 is weakened, so that the plunger 151 moves toward the other permanent magnet against the pressing force of the spring member 161 or with charging the spring member 161. When reverse current flows in the coil 154, the plunger 151 moves to a reverse direction. Therefore, it is possible to reciprocally oscillate the plunger 151 in the axial direction by flowing alternating current in the coil 154.

However, in the above-mentioned conventional reciprocation type linear drive actuator 150, the permanent magnets 155 and 156 are disposed with the clearance with respect to the outer periphery of the plunger, so that inside diameter and outside diameter of the ring shaped permanent magnets 155 and 156 become larger, and volumes of the permanent magnets 155 and 156 also become larger. Following to this, the cost of the permanent magnets 155 and 156 in material becomes expensive. Furthermore, since the permanent magnets 155 and 156 are formed as the ring shape by combination of a plurality of arc-shaped permanent magnets, manufacturing process of the ring shaped permanent magnets 155 and 156 becomes complicated, and the cost of them in manufacturing becomes expensive. As a result, the costs of the actuator using the conventional permanent magnets and coil and the power toothbrush using the same become expensive. Still furthermore, since the permanent magnets 155 and 156 are larger, it is difficult to realize the miniaturization and weight saving of the actuator 150 and the power toothbrush using the same.

DISCLOSURE OF INVENTION

The present invention is done to solve the problems of the above-mentioned conventional ones and purposed to provide a reciprocation type linear driving actuator enabling low cost, miniaturization, weight saving and improvement of assemble workability, and to provide a power toothbrush using the same with low cost, miniaturization and weight saving.

For achieving the above mentioned purpose, a reciprocation type linear driving actuator in accordance with an aspect of the present invention comprises: a moving object having a shaft pivoted to be able to move reciprocally and linearly in an axial direction and permanent magnets each magnetized so that polarities of both end portions in the axial direction of the shaft are different and fitted to be fixed on the shaft; and a stator having a coil disposed to face end faces of the permanent magnets parallel to the axial direction of the shaft with a predetermined clearance and generating magnetic field when current is supplied, thereby reciprocally and linearly moving the moving object in the axial direction of the shaft by supplying alternating current to the coil.

Furthermore, a power toothbrush in accordance with an aspect of the present invention comprises: a brush body that brush is implanted at a front end thereof; a reciprocation type linear driving actuator for driving the brush body reciprocally and linearly in a predetermined direction; an electric power supply for supplying electric power to the reciprocation type linear driving actuator; and a driving circuit for supplying driving current to the reciprocation type linear driving actuator. The reciprocation type linear driving actuator comprises: a moving object having a shaft pivoted to be able to move reciprocally and linearly in an axial direction and permanent magnets each magnetized so that polarities of both end portions in the axial direction of the shaft are different and fitted to be fixed on the shaft; and a stator having a coil disposed to face end faces of the permanent magnets parallel to the axial direction of the shaft with a predetermined clearance and generating magnetic field when current is supplied; and the driving circuit supplies alternating current to the coil thereby reciprocally and linearly moving the moving object in the axial direction of the shaft.

In this way, since the permanent magnets are fitted to be fixed on the shaft, the inside diameter and the outside diameter of the permanent magnets can be made smaller in comparison with a case that the permanent magnets are provided on the stator side. Therefore, volume of the permanent magnet becomes smaller, and cost of the permanent magnet in material can be reduced with following it. Furthermore, since the polarities of both end face portions of the permanent magnet in the axial direction of the shaft are different from each other, the configuration of the permanent magnet becomes simple, it can be easily manufactured, and thereby the cost of the permanent magnet in manufacture can be reduced. Still furthermore, the configuration of the reciprocation type linear driving actuator becomes simple, so that the assembling workability is improved. Consequently, the costs of the reciprocation type linear driving actuator and the power toothbrush using the same can be reduced. Still furthermore, miniaturization and weight saving of the reciprocation type linear driving actuator and the power toothbrush using the same can be realized following to the reduction of the volume of the permanent magnet.

BEST MODE FOR CARRYING OUT THE INVENTION

A reciprocation type linear driving actuator and a power toothbrush using the same in accordance with an embodiment of the present invention are described with reference to drawings.

Figure 1:
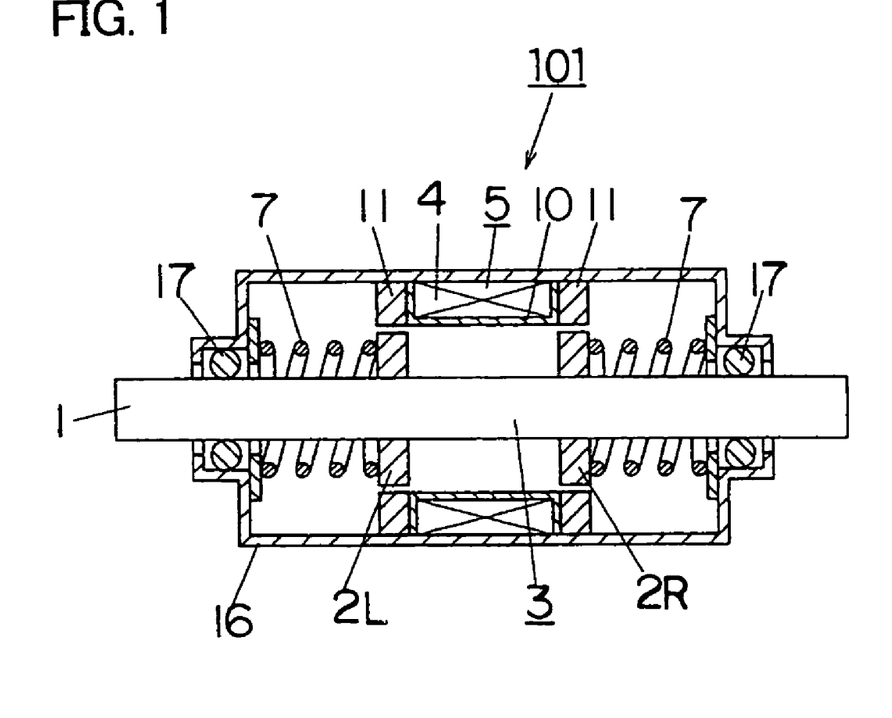
FIG. 1 is a sectional view showing a first constitutional example of a reciprocation type linear driving actuator in accordance with an embodiment of the present invention.

A first constitutional example of the reciprocation type linear driving actuator in accordance with this embodiment is shown in FIG. 1. In the reciprocation type linear driving actuator 101 of the first constitutional example, a stator 5 formed of substantially cylindrical shape is disposed on an inner peripheral surface of a shielding case 16 formed of a tubular shape (for example, cylindrical shape). The stator 5 is configured by a coil 4 formed by winding a wire around a bobbin 10, and stationary yokes 11 of substantially ring shape provided at both sides of the bobbin 10.

Bearings 17 are provided at both end portions in the shielding case 16 in an axial direction thereof, and a shaft 1 fittingly inserted into the shielding case 16 is pivoted by the bearings 17 so as to be movable reciprocally and linearly in the axial direction thereof. Two permanent magnets 2L and 2R of substantially disc shape or substantially tubular shape (for example, circular disc shape or cylindrical shape) are fitted to be fixed on the shaft 1 with a predetermined distance. The shaft 1 and the permanent magnets 2L and 2R constitute a moving object 3.

Besides, in FIG. 1, a thickness, that is, a length in the axial direction of the shaft 1 of the permanent magnets 2L and 2R is shorter than a dimension of the permanent magnets 2L and 2R in a direction perpendicular to the axis of the shaft 1, so that it will be called "disc shape" in the following description. However, the permanent magnets used in the reciprocation type linear driving actuator in accordance with the present invention are not limited to the disc shape and may be tubular shape that the length in the axial direction of the shaft 1 is substantially equal to or longer than the dimension in the direction perpendicular to the axis of the shaft 1.

The permanent magnets 2L and 2R are respectively magnetized in thickness direction, so that polarities at both end face portions in the axial direction of the shaft 1 are set to be different from each other. Furthermore, two permanent magnets 2L and 2R are fixed on the shaft 1 in a manner so that polarities of the faces facing each other become the same. For example, when the polarity at the left end face of the left permanent magnet 2L is assumed as S-pole, the polarity at the right end face of the permanent magnet 2L becomes N-pole, the polarity at the left end face of the right permanent magnet 2R becomes N-pole, and the polarity at the right end face of the permanent magnet 2R becomes S-pole, and vice versa. In this way, it is possible to generate larger magnetic flux by arranging two permanent magnets 2L and 2R in parallel on the shaft 1.

The moving object 3 configured that the permanent magnets 2L and 2R are fitted to and fixed on the shaft 1 is inserted into the shielding case 16 in a manner to be distant with a predetermined clearance with respect to the inner peripheral surface of the stator 5 which is fixed on the shielding case 16. Compression coil spring members 7 are respectively provided that the shaft 1 penetrates each hollow portion thereof between both end faces of the shielding case 16 (or the bearings 17) and two permanent magnets 2L and 2R.

The moving object 3 and the spring members 7 constitute an oscillation system of reciprocal and linear driving of the moving object 3. In other words, the spring members 7 are respectively mediated between both permanent magnets 2L and 2R and the bearings 17, so that two spring members 7 are expanded and contracted by following to the reciprocal linear driving of the moving object 3, and compression force and tensile force are applied to the moving object 3.

Under a state that no current flows in the coil 4, the moving object 3 is stopped at a position where the magnetic force of the permanent magnets 2L and 2R applied to the stationary yoke 11 and forces applied by the spring members 7 are balanced, and outer side faces of two permanent magnets 2L and 2R of the moving object 3 respectively face inner side faces of two stationary yokes 11 of the stator 5.

When a unidirectional current flows in the coil 4, the moving object 3 moves to a direction, and when a reverse current flows in the coil 4, the moving object 3 moves to the reverse direction. Thus, by giving an alternating current flow in the coil 4, the moving object can be driven reciprocally and linearly in the axial direction of the shaft 1. Especially, by flowing an alternating current near to resonance frequency defined by spring constant of the spring members 7 and a mass of the moving object 3 in the coil 4, the reciprocal linear driving (reciprocal oscillation) of the moving object 3 can be made in a state near to resonance oscillation state, thereby the moving quantity (quantity of amplitude) of the moving object 3 can be enlarged.

In this way, in the reciprocation type linear driving actuator 101 in accordance with this embodiment, as for the use of expensive permanent magnets, the disc shaped permanent magnets 2L and 2R are provided on the side of the moving object 3 which is inserted in the stator 5 enabled to be driven reciprocally and linearly instead of providing the permanent magnets on the side of the tubular stator like the conventional one, so that an inside diameter and an outside diameter of the permanent magnets 2L and 2R become smaller, and the volume of the permanent magnets 2L and 2R becomes smaller. Following to this, a cost of the permanent magnet in material can be reduced. Furthermore, since the disc shaped permanent magnets 2L and 2R are respectively magnetized in thickness direction, it is possible to manufacture the disc shaped permanent magnets easily by magnetizing a tubular magnetic substance having predetermined inside diameter and outside diameter in axial direction thereof and cutting it in a direction perpendicular to the center axis thereof with a predetermined thickness. As a result, the cost of the permanent magnet in manufacture can be reduced, too. Still furthermore, since the configuration of the reciprocation type linear driving actuator 101 becomes simple, it is possible to simplify the assembly process thereof. As a result, a cost of the reciprocation type linear driving actuator can be largely reduced. Still furthermore, the reciprocation type linear driving actuator 101 is miniaturized and light weighted in itself due to the volume of the permanent magnets 2L and 2R becomes smaller.

Figure 2:
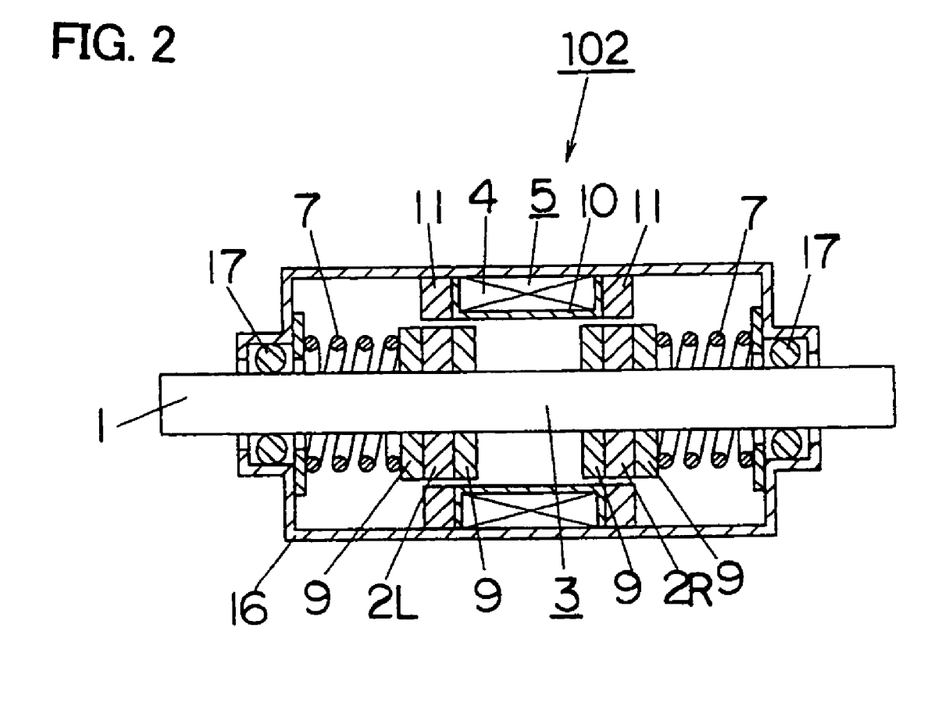
FIG. 2 is a sectional view showing a second constitutional example of the reciprocation type linear driving actuator.

Subsequently, a second constitutional example of a reciprocation type linear driving actuator is shown in FIG. 2. In the reciprocation type linear driving actuator 102 of the second constitutional example, four disc shaped yokes 9 made of magnetic substance are further fitted to and fixed on the shaft 1 in a manner to adjoin both end faces of two permanent magnets 2L and 2R fitted to and fixed on the shaft 1, respectively. In this way, by providing the yokes 9 in a manner to adjoin the end face sides in axial direction of respective permanent magnets 2L and 2R of the moving object 3, most of magnetic flux generated by the permanent magnets 2L and 2R passes the yokes 9. As a result, the configuration becomes a little complex and the cost increases a little in comparison with the reciprocation type linear driving actuator 101 of the first constitutional example, but the magnetic flux of the permanent magnets 2L and 2R can be used efficiently.

Figure 3:
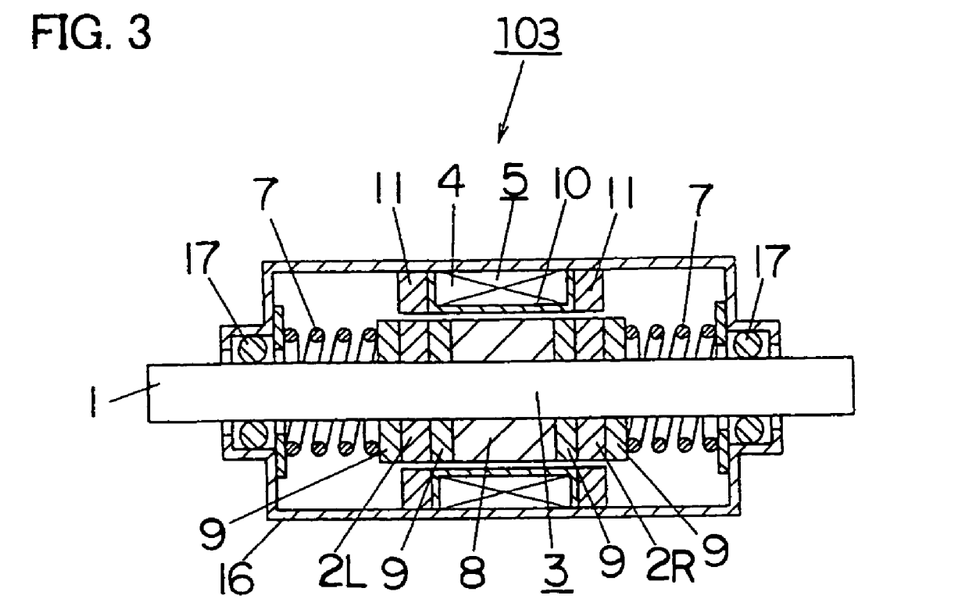
FIG. 3 is a sectional view showing a third constitutional example of the reciprocation type linear driving actuator.

Subsequently, a third constitutional example of a reciprocation type linear driving actuator is shown in FIG. 3. In the reciprocation type linear driving actuator 103 of the third constitutional example, a tubular shaped iron core 8 which serves an a path of magnetic flux generated when a current flows in the coil 4 is further provided between two permanent magnets 2L and 2R. In this way, by providing the tubular shaped iron core 8 between two permanent magnets 2L and 2R, a path serving as a by-pass of the magnetic flux generated by supplying a current to the coil 4 can be formed, so that the magnetic flux generated by the coil 4 can be passed to the permanent magnet 2L and 2R sides of the moving object 3 efficiently, although the configuration further becomes a little complex and the cost increases a little in comparison with the reciprocation type linear driving actuator 102 of the second constitutional example.

Figure 4:
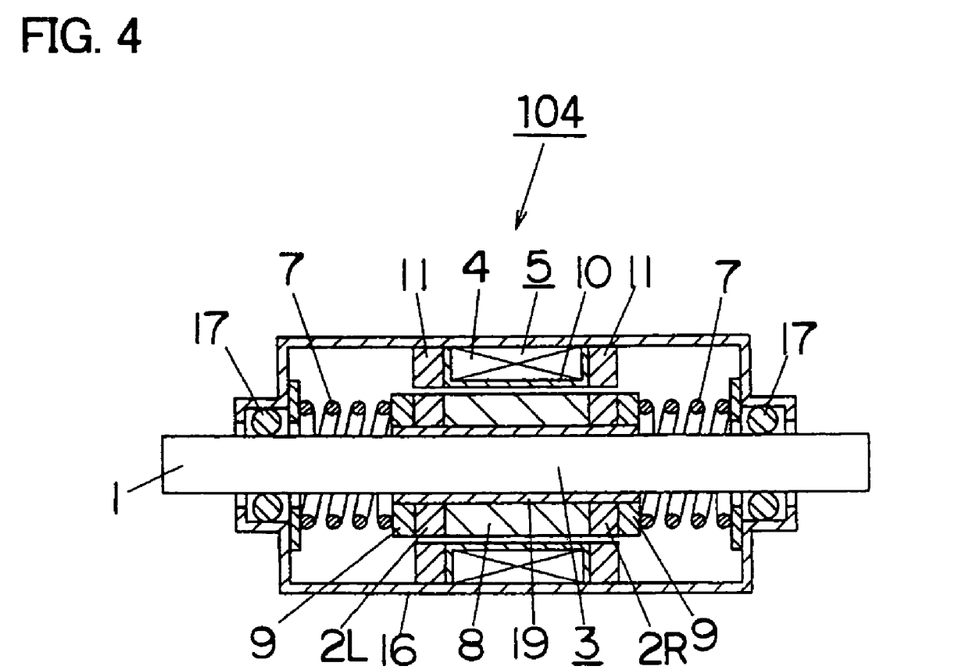
FIG. 4 is a sectional view showing a fourth constitutional example of the reciprocation type linear driving actuator.

Subsequently, a fourth constitutional example of a reciprocation type linear driving actuator is shown in FIG. 4. It is desirable to form the shaft 1 by nonmagnetic material (for example, stainless steel) in order to pass the magnetic flux by the permanent magnets 2L and 2R fitted to and fixed on the shaft 1 to the stationary yokes 11 without passing the shaft 1. The nonmagnetic material, however, is generally expensive in comparison with the magnetic material. Furthermore, inexpensive nonmagnetic material has low strength. In the reciprocation type linear driving actuator 104 of the fourth constitutional example, the shaft 1 is made of a magnetic material such as iron, and a tubular shaped spacer 19 made of a nonmagnetic material is fitted to and fixed on the shaft 1. Furthermore, the permanent magnets 2L and 2R, the yokes 9 and the iron core 8 are fitted to and fixed on an outer peripheral surface of the spacer.

In this way, by mediating the spacer 19 made of the nonmagnetic material, the shaft 1 can be formed with using a magnetic material of inexpensive and high strength although the configuration becomes a little complex, so that it is possible to reduce the cost with maintaining the strength of the shaft 1. Furthermore, the magnetic flux by the permanent magnets 2L and 2R can pass to the stationary yokes 11 efficiently.

Figure 5:
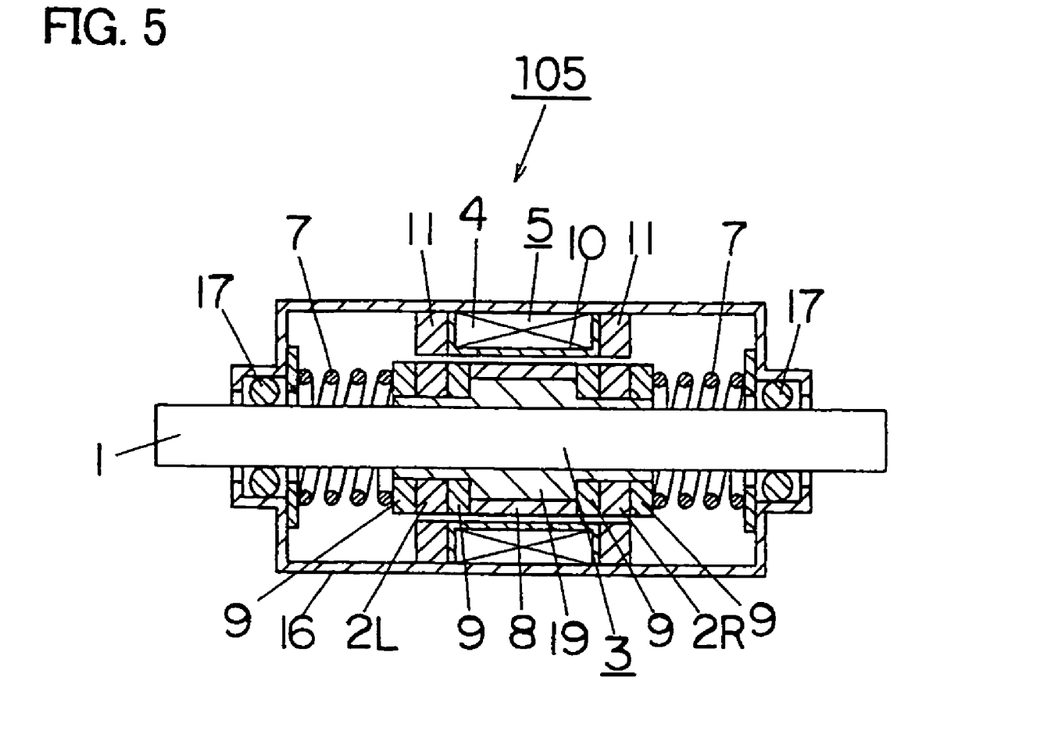
FIG. 5 is a sectional view showing a fifth constitutional example of the reciprocation type linear driving actuator.

Subsequently, a fifth constitutional example of a reciprocation type linear driving actuator is shown in FIG. 5. For forming the shortest magnetic path on forming a passage way (magnetic path) of magnetic flux generated by the coil 4 with using the tubular iron core 8, it is necessary to make the outside diameter of the iron core 8 substantially equal to the outside diameter of the permanent magnets 2L and 2R or the yokes 9. On the other hand, the inside diameter of the iron core 8 is not necessarily made substantially equal to the inside diameter of the permanent magnets 2L and 2R or the yokes 9. Rather when the inside diameter of the iron core 8 is set to be the same as the inside diameter of the permanent magnets 2L and 2R or the yokes 9, the weight of the iron core 8 becomes heavier. Thus, it is not preferable because the weight ob the moving object 3 becomes heavier too, consequently. Therefore, in the reciprocation type linear driving actuator 105 of the fifth constitutional example, the inside diameter of the iron core 8 is made larger than the inside diameter of the permanent magnets 2L and 2R or the yokes 9, and an outside diameter of a portion of the spacer 19 made of nonmagnetic material where the iron core 8 is fitted and fixed, that is, the center portion in the axial direction is made larger than a diameter of another portion.

In this way, the weight of the iron core 8 can be lightened by raising the inside diameter of the iron core 8 than the inside diameter of the permanent magnets 2L and 2R or the yokes 9, although the shape of the spacer 19 becomes a little complex, and, consequently, the moving object 3 can be light-weighted. Furthermore, the magnetic path through which the magnetic flux generated by the coil 4 can be made the shortest length, so that the magnetic flux generated by the coil 4 can be utilized effectively.

Figure 6:
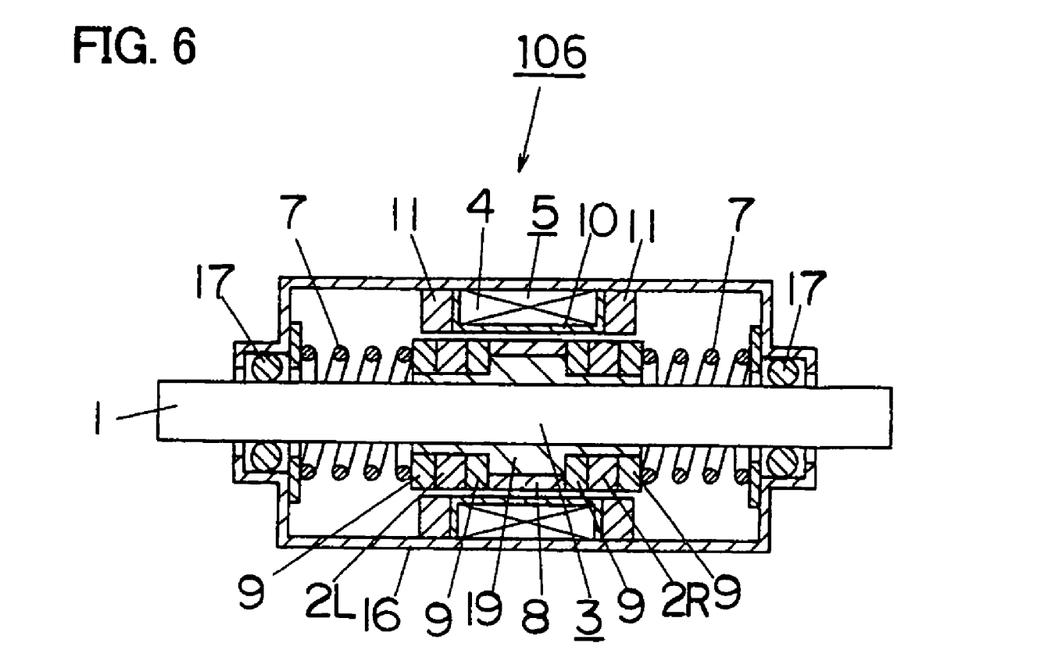
FIG. 6 is a sectional view showing a sixth constitutional example of the reciprocation type linear driving actuator.
Figure 7:
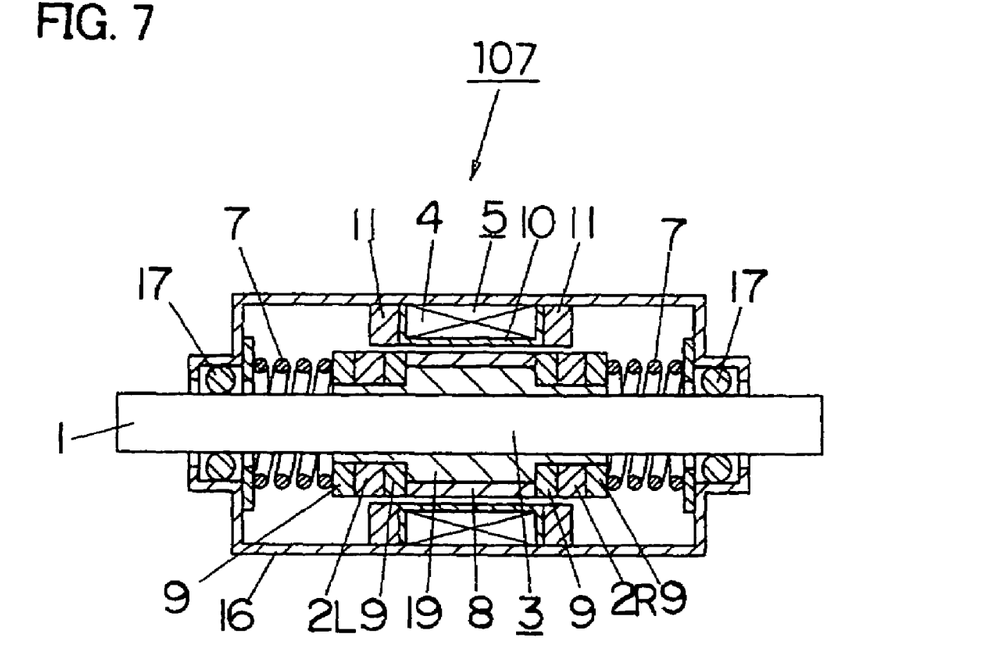
FIG. 7 is a sectional view showing a seventh constitutional example of the reciprocation type linear driving actuator.

Subsequently, a sixth constitutional example of a reciprocation type linear driving actuator is shown in FIG. 6 and a seventh constitutional example is shown in FIG. 7, respectively. In the reciprocation type linear driving actuator 106 of the sixth constitutional example, a distance between two permanent magnets 2L and 2R fitted to and fixed on the moving object 3 is made narrower than a distance between two stationary yokes 11 of the stator 5, and the center position between two stationary yokes 11 in the axial direction is substantially coincided with the center position between two permanent magnets 2L and 2R when the moving object 3 is not in the reciprocal linear driving state.

On the other hand, in the reciprocation type linear driving actuator 107 of the seventh constitutional example, a distance between two permanent magnets 2L and 2R fitted to and fixed on the moving object 3 is made wider than a distance between two stationary yokes 11 of the stator 5, and the center position between two stationary yokes 11 in the axial direction is substantially coincided with the center position between two permanent magnets 2L and 2R when the moving object 3 is not in the reciprocal linear driving state.

By setting the distance between two permanent magnets 2L and 2R narrower or wider than the distance of two stationary yokes 11, the stroke of the reciprocal linear driving or the amplitude of the reciprocal oscillation of the moving object 3 cab be adjusted corresponding to the use.

Furthermore, by substantially coinciding the center position between two stationary yokes 11 in the axial direction with the center position between two permanent magnets 2L and 2R when the moving object 3 is not in the reciprocal linear driving state, tensile force and reaction force due to the permanent magnets 2L and 2R against the stationary yokes 11 at a neutral position of the amplitude can be made zero, so that the design of the spring members 7 becomes easier, and the assemble workability of the reciprocation type linear driving actuator is increased.

Figure 8:
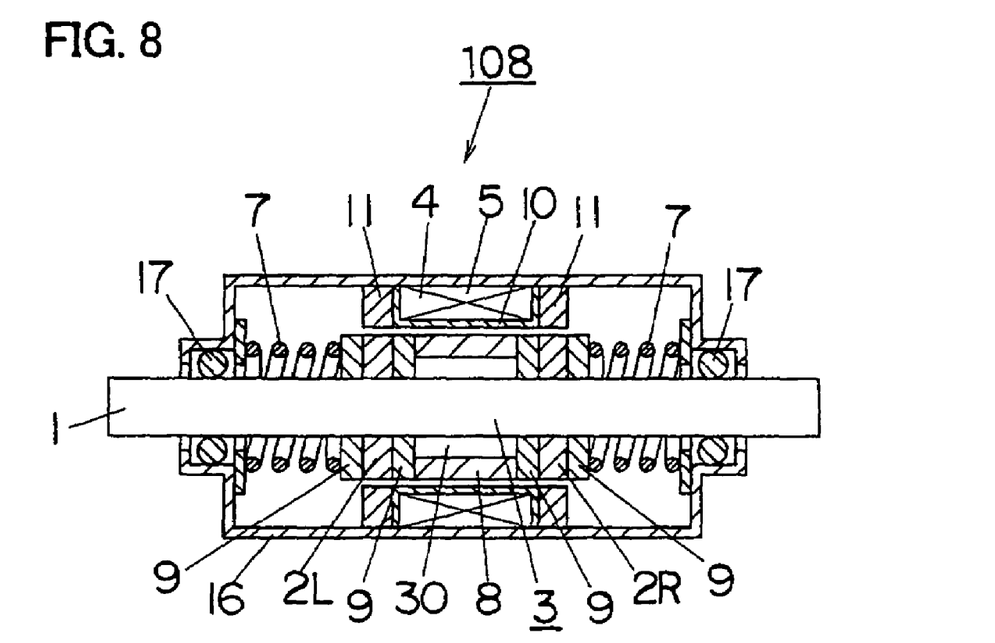
FIG. 8 is a sectional view showing an eighth constitutional example of the reciprocation type linear driving actuator.

Subsequently, an eighth constitutional example of a reciprocation type linear driving actuator is shown in FIG. 8. In the reciprocation type linear driving actuator 108 of the eighth constitutional example, the permanent magnets 2L and 2R and the yokes 9 are directly fitted to and fixed on the shaft 1 without using the spacer 19, and a space 30 is formed between the inner peripheral surface of the tubular iron core 8 and the outer peripheral surface of the shaft 1. According to such a configuration, the iron core 8 can be fixed relatively easier with using a jig or the like, so that the moving object 3 can be light-weighted with making the assembly process not that much.

Figure 9A:
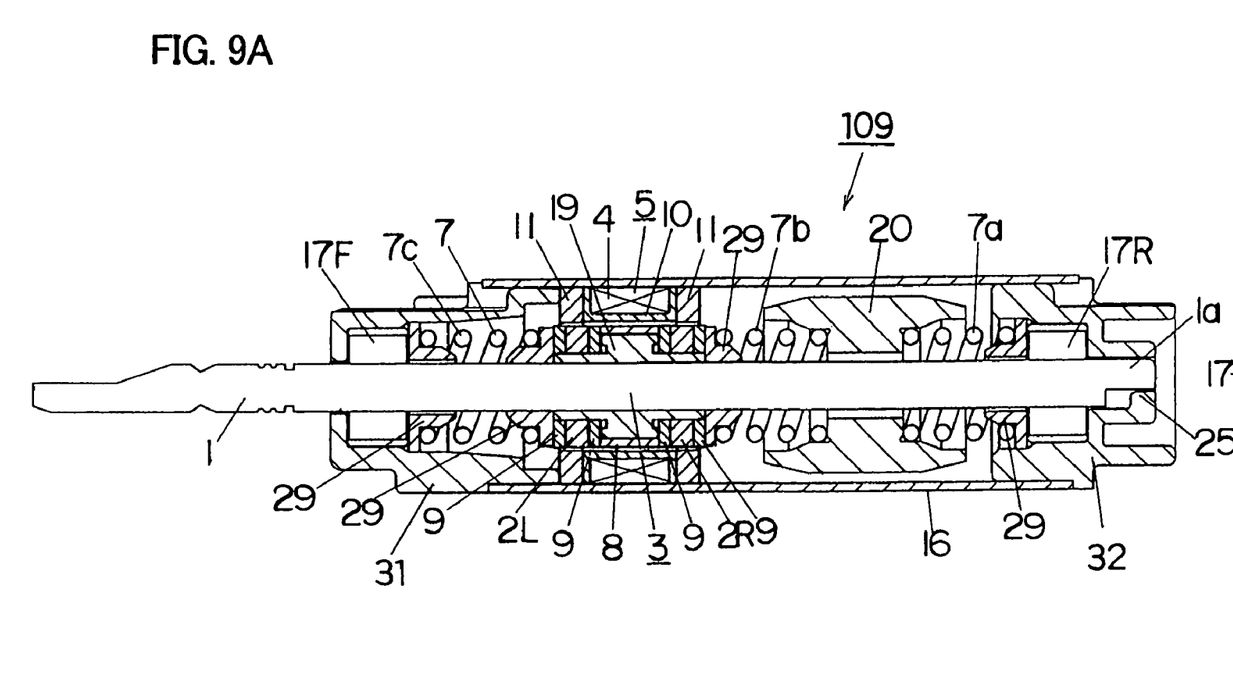
FIG. 9A is a sectional view showing a configuration of a reciprocation type linear driving actuator in accordance with another embodiment of the present invention.
Figure 9B:
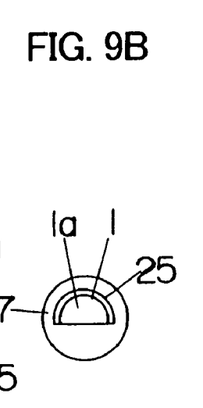
FIG. 9B is a view showing an example of positioning structure for positioning a moving object of the reciprocation type linear driving actuator shown in FIG. 9A around a shaft.
Figure 10:
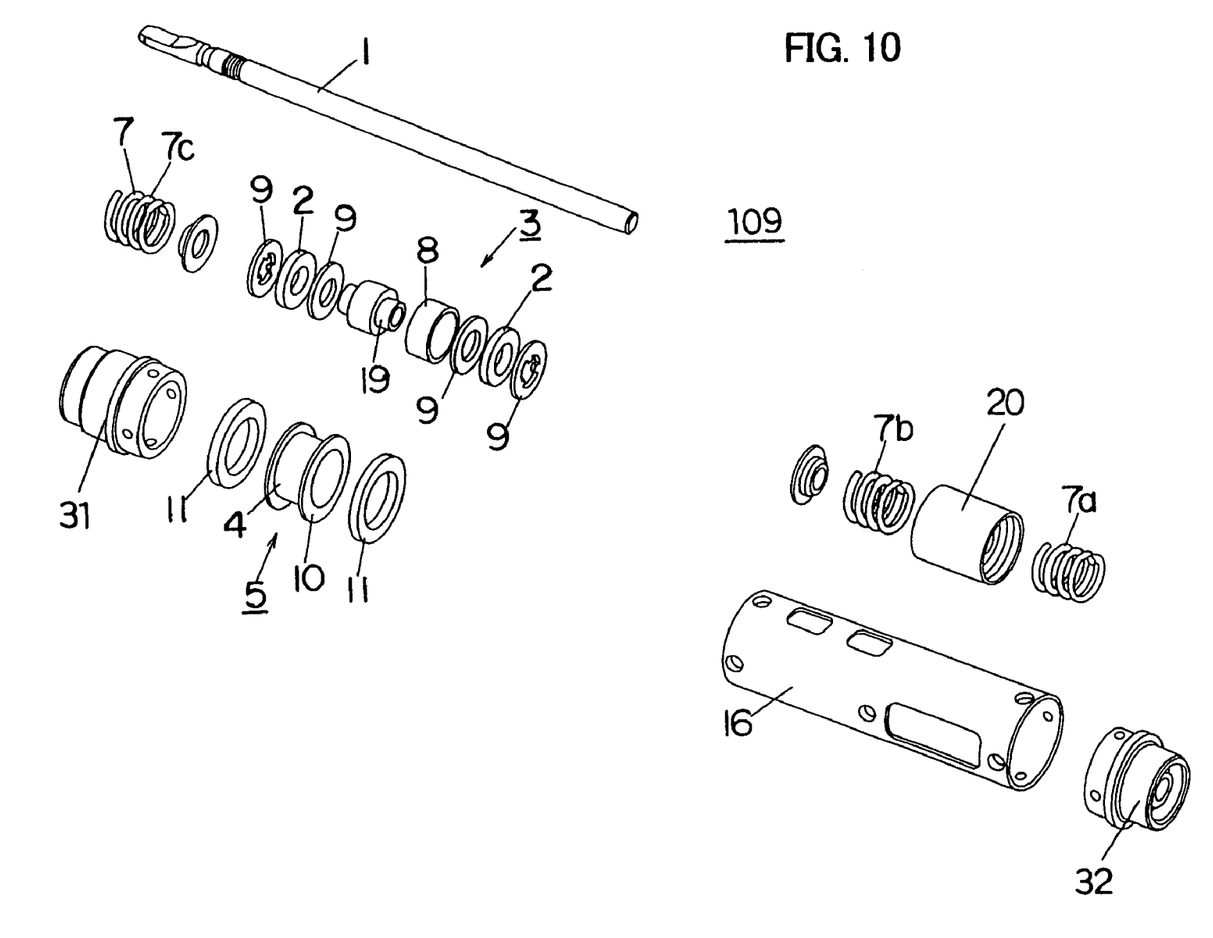
FIG. 10 is an exploded perspective view of the reciprocation type linear driving actuator shown in FIG. 9A.

Subsequently, more specific constitutional example of the reciprocation type linear driving actuator which is considered to be used as an actuator of power toothbrush is described. FIG. 9A is a sectional drawing showing a configuration of the reciprocation type linear driving actuator 109 used as an actuator of power toothbrush. In the reciprocation type linear driving actuator 109, as for the moving object 3 and the stator 5, things similar to the above-mentioned sixth constitutional example are used, but they are mot limited to those, it is possible to use any one in the first to eighth constitutional examples. FIG. 9B is a view showing shapes of a rear end portion of the shaft 1 and a bearing for pivoting it of the reciprocation type linear driving actuator 109. FIG. 10 is an exploded perspective view showing the configuration of the reciprocation type linear driving actuator 109.

As can be seen from FIG. 9A and FIG. 10, a shielding case 16 has a substantially tubular shape, and sealing members 31 and 32 are respectively fitted and fixed to front and rear openings thereof. Furthermore, bearings 17F and 17R for pivoting the shaft 1 capable of reciprocal linear driving in the axial direction thereof are respectively provided on the sealing members 31 and 32. As shown in FIG. 9B, a cross section of a rear end portion 1a of the shaft 1 is formed to be substantially D-shape. On the other hand, a fitting hole 25 of substantially D-shape into which the rear end portion 1a of the shaft 1 is fitted is formed on the sealing member 32 in rear side. Since the rear end portion 1a of the shaft 1 is fitted into the fitting hole 25, the shaft 1 can be driven reciprocally and linearly in the axial direction thereof but the rotation around the axis thereof is restricted. In addition, it is possible to restrict the rotation of the shaft 1 around the axis thereof in the above-mentioned reciprocation type linear driving actuator in the first constitutional example to the eighth constitutional example, similarly.

The stator 5 is fixed on an inner peripheral surface of the shielding case 16. In addition, the moving object 3 is fitted to and fixed on the shaft 1 so that the outer peripheral surface thereof faces the inner peripheral surface of the stator 5 with a predetermined clearance. Spring receiving members 29 are respectively fitted to the shaft 1 so as to face a rear face of the bearing 17F in front side, front and rear face of the moving object 3 and a front face of the bearing 17R in rear side. Furthermore, a vibrational absorption spindle 20 having a substantially tubular shape is engaged with the shaft 1 with relatively larger allowance between the moving object 3 and the bearing 17R in rear side. Then, coil springs 7a and 7b are respectively provided between the spring receiving members 29 and the vibrational absorption spindle 20, and a coil spring 7c is provided between the spring receiving members 29 of the moving object 3 and the bearing 17F in front side.

In this embodiment, the stator 5 and the shielding case 16 are assumed stationary portion, and it can be handled as a system of two mass point vibration model of mass of the moving object 3 and mass of the vibrational absorption spindle 20. In this case, there are the first (low-order side) oscillation mode that moving object 3 and the vibrational absorption spindle 20 are driven in the same phase and the second (high-order side) oscillation mode that the moving object 3 and the vibrational absorption spindle 20 are driven in opposite phase. When the moving object 3 is driven reciprocally and linearly in the axial direction by supplying a current having a frequency near to natural vibration frequency in the second vibration mode to the coil 4, the vibrational absorption spindle 20 which is driven in opposite phase cancels inertial force of the moving object 3, and in reverse, the moving object 3 cancels inertial force of the vibrational absorption spindle 20. Thereby, the vibration propagated to the shielding case 16 can be reduced.

Figures 11A, 11B:
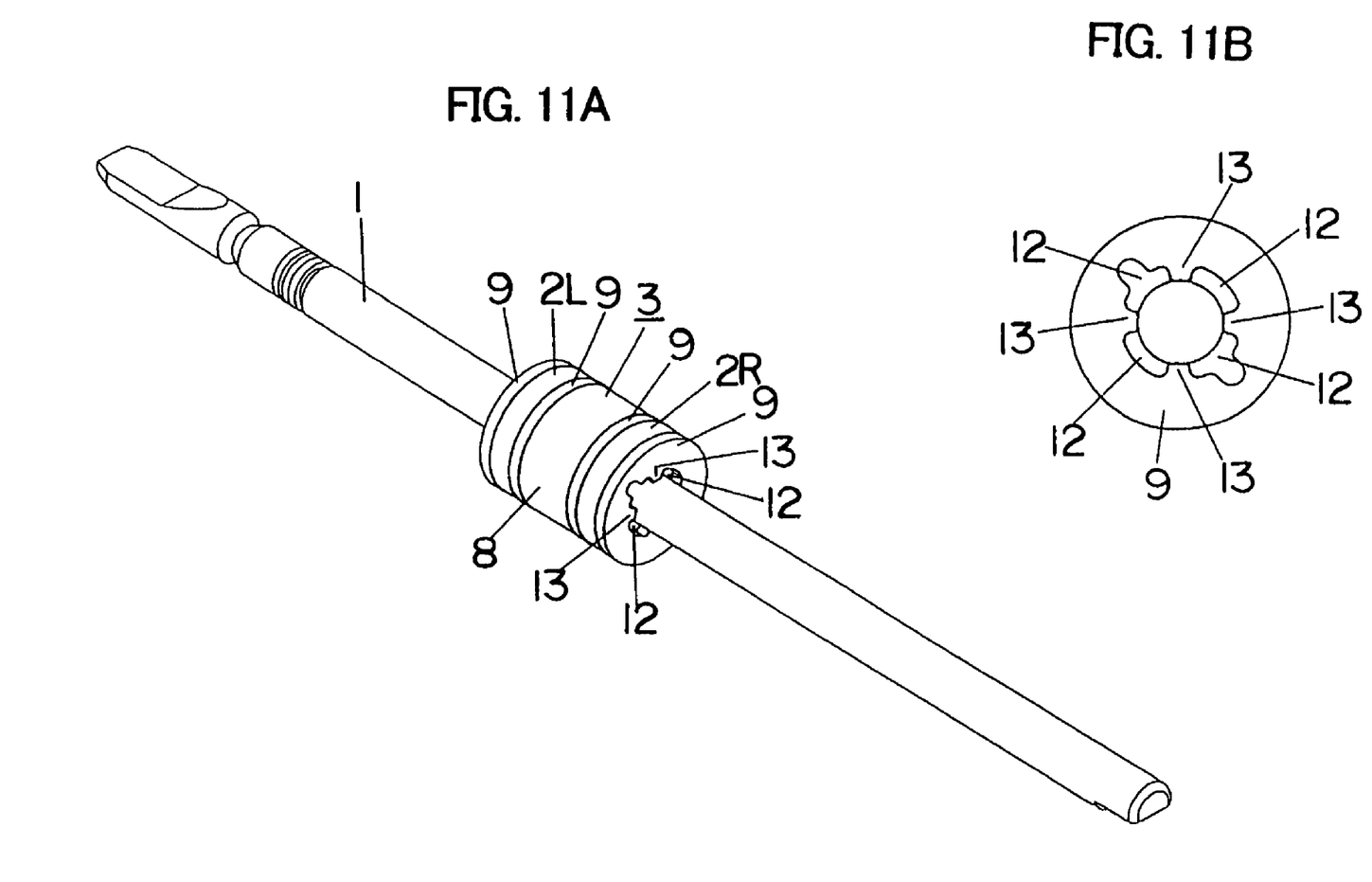
FIG. 11A is a perspective view showing a modification of a structure for fitting and fixing permanent magnets and yokes on a shaft in the above-mentioned another embodiment.
FIG. 11B is a front view showing a shape of the above yoke.

Subsequently, a modified example of a structure for fitting and fixing the permanent magnets 2L and 2R and the yokes 9 to and on the shaft 1 is shown in FIG. 11A and FIG. 11B. In the constitutional example shown in FIG. 9A and FIG. 10, the spacer is fitted to the shaft 1 made of a magnetic material, and the permanent magnets 2L and 2R and the yokes 9 are further fitted to and fixed on the spacer 19. In the modified example shown in FIG. 11A and FIG. 11B, a plurality of (for example, four) protrusions 13 is formed on an inner peripheral portion of the yokes 9, the yokes 9 are fitted to and fixed on the shaft 1 by contacting the protrusions 13 to the outer peripheral surfaces of the shaft 1, and gaps 12 are formed between respective protrusions 13. It is not illustrated, but the same does for respective permanent magnets 2L and 2R. As a result, the magnetic flux by the permanent magnets 2L and 2R rarely passes through the shaft 1 side and most of it can be passed through the stationary yokes 11 side, and the magnetic flux by the permanent magnets 2L and 2R can be utilized effectively, although the shaft 1 is made of the magnetic material for reducing cost and for ensuring strength of the shaft 1.

Figure 12:
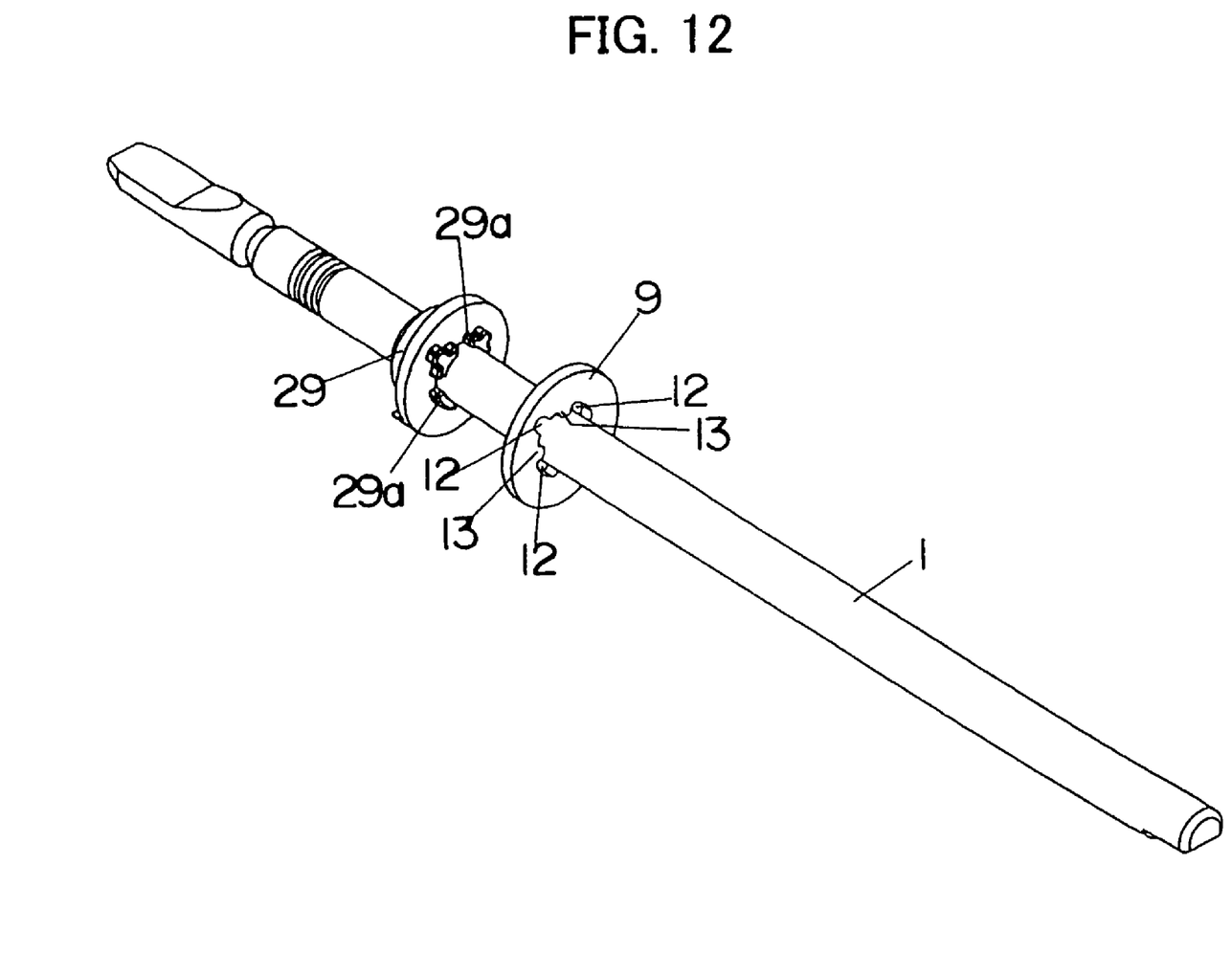
FIG. 12 is a perspective view showing a coupling state of a spring carrier member with the above yoke.

Furthermore, as shown in FIG. 12, a plurality of (for example, four) engaging protrusions 29a is formed on an end face of the spring receiving members 29 which is not contact with the spring member 7a, 7b or 7c so as to be fitted to the gaps 12 formed on the yokes 9. By such a configuration, the rotation of the spring receiving members 29 with respect to the yokes 9 around the center axis of the shaft 1 can be restricted.

Subsequently, a relationship between frequency and amplitude of the moving object 3 when a voltage of alternating current supplied to the coil 4 is set to be constant, and a relationship between the frequency and current at that time in the reciprocation type linear driving actuator in accordance with this embodiment are described with reference to a graph shown in FIG. 13.

Figure 13:
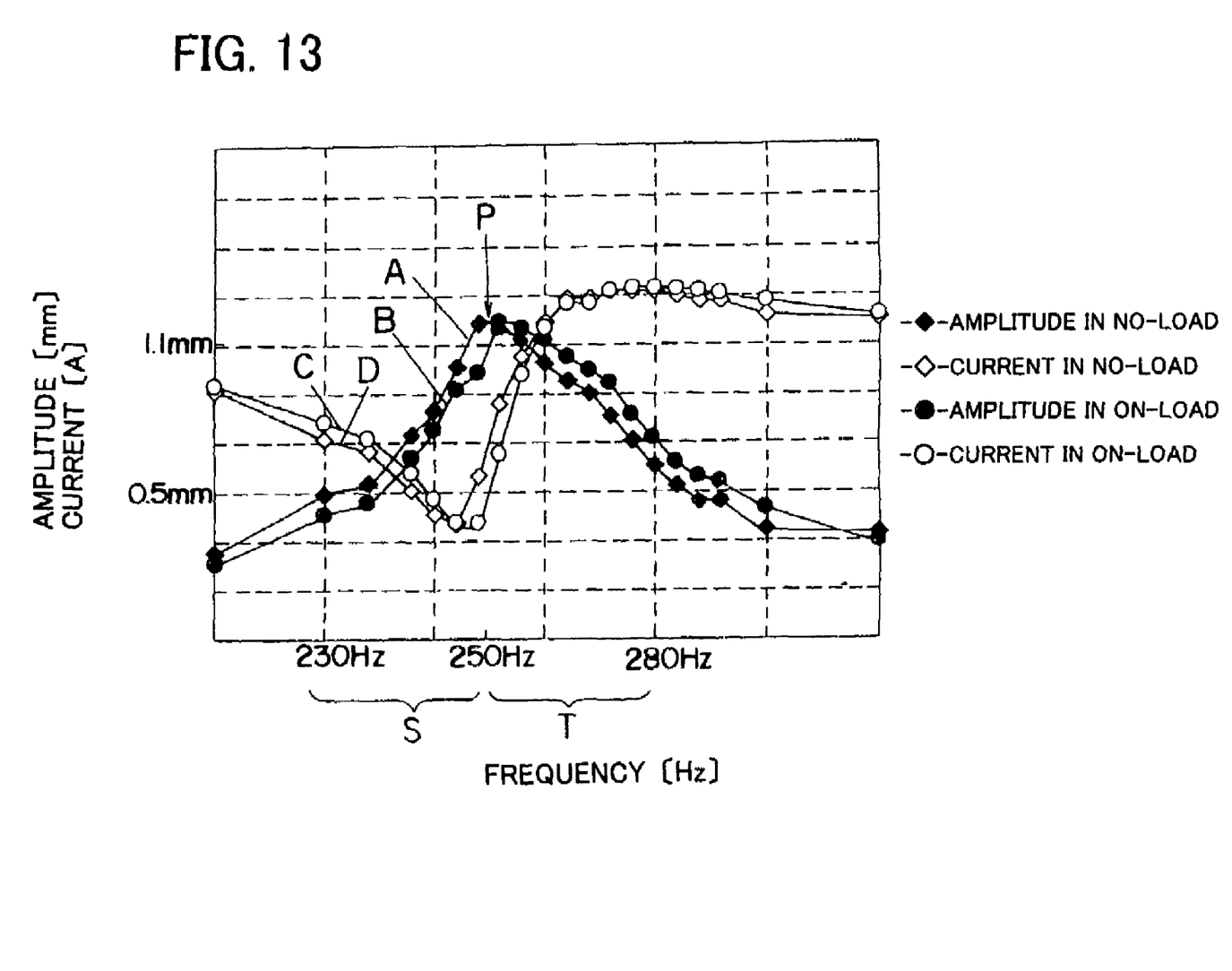
FIG. 13 is a graph showing a relation between frequency of alternating current and amplitude of the moving object when voltage is made to be constant in the reciprocation type linear driving actuator and a relation between the frequency and current at that time.

In FIG. 13, curves A and B respectively show the relationship between frequency and amplitude of the moving object 3 when the voltage is set to be constant, and curves C and D respectively show the relationship between the frequency and current. In FIG. 13, a mark ♦ designates amplitude in no-load, a mark ● designates amplitude in on-load, a mark ◇ designates current value in no-load, and a mark ○ designates current value in no-load, respectively.

As mentioned before, the oscillation quantity (amplitude quantity) of the moving object 3 can be increased by supplying the alternating current having a frequency near to the resonance vibration frequency (shown by point P in FIG. 13) defined by the spring constant of the spring members 7a, 7b and 7c and the mass of the moving object 3 to the coil 4. For example, in the vicinity of frequency 250 Hz, the amplitude of the moving object 3 shows the maximum value 1.1 mm. In the region S of the frequency equal to or larger than 230 Hz and equal to or smaller than 250 Hz and in the region T equal to or larger than 250 Hz and equal to or smaller than 280 Hz, the amplitude shows a value equal to or larger than 0.5 mm, respectively.

When the frequency of the alternating current flowing to the coil 4 is set in these regions, it is possible to enlarge the oscillation quantity (amplitude quantity) of the moving object 3 with utilizing the spring members 7a, 7b and 7c. Hereupon, in the vicinity of the resonance vibration frequency, and in a region of frequency higher than the resonance vibration frequency and in a region of frequency lower than the resonance vibration frequency, amplitude similar to this can be obtained. When the moving object 3 is driven reciprocally and linearly by setting the frequency lower than the resonance vibration frequency (when the frequency is set in the region S), it is possible to perform the reciprocal linear driving with the aimed amplitude by small current. Especially, when a power supply of the reciprocation type linear driving actuator is a battery, it is possible to make the operation life of the battery longer. On the other hand, when the frequency is set to be higher than the resonance vibration frequency (when the frequency is set in the region T), although the current becomes larger, it is possible to perform the reciprocal linear driving with the aimed amplitude so as to take a large output power.

The above-mentioned each reciprocation type linear driving actuator can be used as various kinds of driving force. As an example, a configuration of a power toothbrush comprising the above-mentioned reciprocation type linear driving actuator is shown in FIG. 14.

The power toothbrush 100 comprises a tubular shaped slender housing 15, a reciprocation type linear driving actuator 109 shown in above FIG. 9A provided in front side in the housing 15 in longitudinal direction, a battery (secondary battery) 21 provided in rear side in the housing 15 in the longitudinal direction, a control circuit unit 22, an electric switch 33 provided on an outer periphery portion of the housing 15, and so on. An end portion of the shaft 1 of the reciprocation type linear driving actuator 109 is protruded outward from a front end face of the housing 15.

Figure 14:
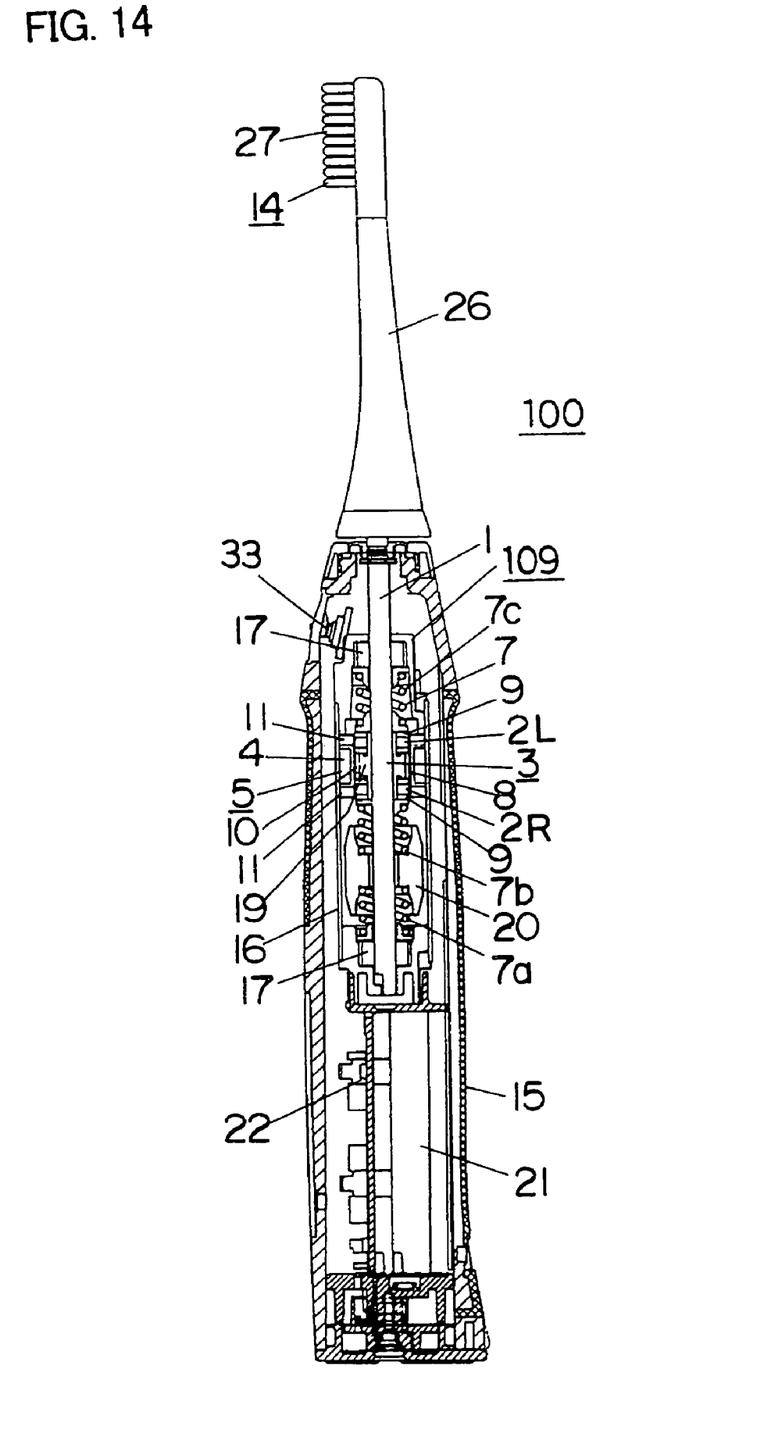
FIG. 14 is a sectional view showing a configuration of a power toothbrush using the reciprocation type linear driving actuator in accordance with an embodiment of the present invention.

In the example shown in FIG. 14, since a brush body 14 is a type that a brush portion 27 at a front end thereof is implanted in a direction substantially perpendicular to longitudinal direction of the brush body 14, it is attached on the shaft 1 in a manner so that a rear end portion of a handle portion 26 of the brush body 14 is detachably attached on an end of the shaft 1, and not rotatable around the axis of the shaft 1. In the reciprocation type linear driving actuator 109 shown in FIG. 9A, the rear end portion 1a of the shaft 1 is formed to be substantially D-shape, and the fitting hole 25 into which the rear end portion 1a is fitted is formed to be substantially D-shape, too, so that the rotation of the shaft 1 around the axis thereof is restricted. Thus, by forming the handle portion 26 of the brush body 14 and the front end portion of the shaft 1 to be similar structure, it is possible to restrict the handle portion 26 not to rotate around the axis of the shaft 1. As a result, a positional relationship between the protruding direction of the brush portion 27 of the brush body 14 and the electric switch 33 provided on the housing 15 can be made constant, so that operability as the power toothbrush may not be failed. When the electric switch 33 of the power toothbrushes 100 which is configured as above is operated to supply a current to the coil 4 of the reciprocation type linear driving actuator 109, the shaft 1 can be driven reciprocally and linearly in the axial direction thereof. Thereby, the brush body 14 attached on the shaft 1 is driven reciprocally and linearly in the axial direction, so that brushing of teeth can be performed by driving the brush portion 27 reciprocally and linearly.

As mentioned above, according to each configuration of the reciprocation type linear driving actuator in accordance with this embodiment, the permanent magnets 2L and 2R of substantially disc shape or substantially tubular shape (circular disc shape or cylindrical shape) are fitted to and fixed on the shaft 1 directly or via the spacer 19, so that the inside diameter and the outside diameter of respective permanent magnets 2L and 2R become smaller, and the volume of the permanent magnets 2L and 2R becomes smaller. Following to this, the weight and cost of the permanent magnet are reduces, consequently, the costs of the reciprocation type linear driving actuator and the power toothbrush using the same can be reduced.

This application is based on Japanese patent application 2003-139571 filed in Japan, the contents of which are hereby incorporated by references of the specification and drawings of the above patent application.

Although the present invention has been fully described by way of example with reference to the accompanying drawings, it is to be understood that various changes and modifications will be apparent to those skilled in the art. Therefore, unless otherwise such changes and modifications depart from the scope of the present invention, they should be construed as being included therein.

INDUSTRIAL APPLICABILITY

As mentioned above, in the reciprocation type linear driving actuator of the present invention, the inside diameter and outside diameter of the permanent magnet become smaller, and the volume of the permanent magnet becomes smaller. Corresponding to this, the cost of the permanent magnet in material can be reduced. Furthermore, since the permanent magnet is magnetized so that polarities at both end faces in axial direction are different each other, the configuration of the permanent magnet is simple and manufacture of it becomes easy, and the cost of the permanent magnet in manufacture can be reduced. Still furthermore, the configuration of the reciprocation type linear driving actuator becomes simple, so that assemble workability can be increased. As a result, the cost of the reciprocation type linear driving actuator can be reduced largely. Still furthermore, corresponding to the reduction of the volume of the permanent magnet, the reciprocation type linear driving actuator can be miniaturized and light-weighted. Still furthermore, since the power toothbrush of the present invention uses the reciprocation type linear driving actuator of low cost, miniaturized and light-weighted as mentioned above, the miniaturized and light-weighted power toothbrush can be provided in low cost.

The invention claimed is:

1. A reciprocation type linear driving actuator comprising:
   a moving object having a shaft pivoted to move reciprocally and linearly in an axial direction, and two permanent magnets each magnetized so that polarities of both end portions in the axial direction of the shaft are different, the two permanent magnets are configured to be fixed on the shaft with a predetermined distance between the two permanent magnets in the axial direction of the shaft; and
   a stator having a coil disposed between the two permanent magnets in the axial direction of the shaft in a normal condition when no current is supplied thereto, the coil being adjacent end faces of the two permanent magnets parallel to the axial direction of the shaft with a predetermined clearance, the stator generating a magnetic field for driving the moving object reciprocally and linearly in the axial direction of the shaft when alternating current is supplied.

2. The reciprocation type linear driving actuator in accordance with claim 1, wherein the moving object has an iron core having a substantially tubular shape fitted to the shaft so as to be parallel to the axial direction of the shaft between the two permanent magnets; and
   the two permanent magnets are magnetized in a thickness direction thereof so that polarities of both end faces of each permanent magnet are different from each other in the axial direction of the shaft, and fixed on the shaft so that the polarity of an end face of one of the two permanent magnets facing an end face of the second of the two permanent magnet is the same.

3. The reciprocation type linear driving actuator in accordance with claim 2, wherein a plurality of yokes are fixed on the shaft so as to adjoin each end face of the two permanent magnets in the axial direction of the shaft.

4. The reciprocation type linear driving actuator in accordance with claim 3, wherein an inside diameter of the iron core is larger than an inner diameter of the two permanent magnets or the yokes.

5. The reciprocation type linear driving actuator in accordance with claim 1, wherein the shaft is made of a nonmagnetic material.

6. The reciprocation type linear driving actuator in accordance with claim 1, wherein the shaft is made of a magnetic material, and the shaft and the two permanent magnets are fixed with a spacer made of a nonmagnetic material.

7. The reciprocation type linear driving actuator in accordance with claim 2, wherein the stator further has a bobbin around which the coil is wound, and two stationary yokes provided at sides of the bobbin in the axial direction of the shaft; and
   a distance between the two permanent magnets fixed on the moving object is narrower than a distance between the two stationary yokes of the stator, and a center position between the two stationary yokes in the axial direction is substantially coincided with a center position between the two permanent magnets when the moving object is not driven reciprocally and linearly.

8. The reciprocation type linear driving actuator in accordance with claim 3, wherein the plurality of yokes includes a plurality of protrusions and a plurality of gaps between each respective protrusion at an inner peripheral surface of each of the plurality of yokes, the plurality of protrusions being configured to contact an outer peripheral surface of the shaft.

9. The reciprocation type linear driving actuator in accordance with claim 1 further comprising:
   a member that restricts rotation of the moving object around the axis of the shaft.

10. The reciprocation type linear driving actuator in accordance with claim 1 further comprising:
    spring members coupled with the moving object for supporting the moving object capable of reciprocal linear driving in the axial direction of the shaft, and wherein a vibration system of reciprocal linear driving in the axial direction of the shaft is composed of the moving object and the spring members; and
    the moving object is reciprocally and linearly driven by an alternating current flowing through the coil having a frequency equal to or near to a resonance vibration frequency of the vibration system of reciprocal linear driving.

11. The reciprocation type linear driving actuator in accordance with claim 1 further comprising:
    spring members coupled with the moving object for supporting the moving object capable of reciprocal linear driving in the axial direction of the shaft, and wherein a vibration system of reciprocal linear driving in the axial direction of the shaft is composed of the moving object and the spring members; and
    the moving object is reciprocally and linearly driven by an alternating current flowing through the coil having a frequency near to and lower than a resonance vibration frequency of the vibration system of reciprocal linear driving.

12. The reciprocation type linear driving actuator in accordance with claim 1 further comprising:
    spring members coupled with the moving object for supporting the moving object capable of reciprocal linear driving in the axial direction of the shaft, and wherein a vibration system of reciprocal linear driving in the axial direction of the shaft is composed of the moving object and the spring members; and
    the moving object is reciprocally and linearly driven by an alternating current flowing through the coil having a frequency near to and higher than a resonance vibration frequency of the vibration system of reciprocal linear driving.

13. A power toothbrush comprising: a brush body that brush is implanted at a front end thereof; a reciprocation type linear driving actuator for driving the brush body reciprocally and linearly in a predetermined direction; an electric power supply for supplying electric power to the reciprocation type linear driving actuator; and a driving circuit for supplying driving current to the reciprocation type linear driving actuator, wherein
    the reciprocation type linear driving actuator comprises:
    a moving object having a shaft pivoted to move reciprocally and linearly in an axial direction, and two permanent magnets each magnetized so that polarities of both end portions in the axial direction of the shaft are different, the two permanent magnets are configured to be fixed on the shaft with a predetermined distance between the two permanent magnets in the axial direction of the shaft; and
    a stator having a coil disposed between the two permanent magnets in the axial direction of the shaft in a normal condition when no current is supplied thereto, the coil adjacent end faces of the two permanent magnets parallel to the axial direction of the shaft with a predetermined clearance, stator generating a magnetic field for driving the moving object reciprocally and linearly in the axial direction of the shaft when alternating current is supplied from the driving circuit.

* * * * *